US005503143A

United States Patent [19]

Marion et al.

[11] Patent Number: 5,503,143

[45] Date of Patent: Apr. 2, 1996

[54] METHOD AND APPARATUS FOR REMOVING LIQUID FROM A PATIENT'S LUNGS

[76] Inventors: Joseph Marion, c/o Mrs. Diane Giampaoli, 162 Maywood Way, San Rafael, Calif. 94901; Melvin R. Maglio, Jr., P.O. Box 835, Crescent City, Calif. 95531; Michael Marion, 1018 Mission St., San Francisco, Calif. 94103

[21] Appl. No.: 197,699

[22] Filed: Feb. 17, 1994

[51] Int. Cl.[6] ............................ A61G 10/00; A61M 15/00

[52] U.S. Cl. ................................ 128/202.12; 128/205.26; 128/203.12; 128/205.15

[58] Field of Search ......................... 128/202.12, 203.12, 128/204.23, 205.15, 205.28, 205.26, 205.19, 204.18; 600/21, 22

[56] References Cited

U.S. PATENT DOCUMENTS

| | | | |
|---|---|---|---|
| 2,385,683 | 9/1945 | Burton | 128/202.12 |
| 2,448,546 | 9/1948 | Plemel et al. | 205/26 |
| 3,396,725 | 8/1968 | Schreiber | 128/205.19 |
| 3,523,561 | 8/1970 | Galeazzi | 128/205.26 |
| 3,527,202 | 9/1970 | Donzelle | 600/21 |
| 3,547,118 | 12/1970 | Kolman et al. | 128/205.26 |
| 4,633,859 | 1/1987 | Reneau | 128/205.26 |
| 5,101,819 | 4/1992 | Lane | 128/205.26 |
| 5,368,067 | 11/1994 | Cook, Jr. | 137/485 |

*Primary Examiner*—Edgar S. Burr
*Assistant Examiner*—V. Srivastava
*Attorney, Agent, or Firm*—Bruce H. Johnsonbaugh

[57] ABSTRACT

A hypobaric chamber apparatus and method are provided for removing excess fluid from the lungs of a patient. A cylindrical vessel is used having a hatch at one end to allow entry of a patient into the chamber. A patient is placed in the chamber and breathes oxygen-rich gas through a face mask while a vacuum pump reduces the pressure in the chamber to a predetermined pressure between 2 and 10 psi. A helium purge system is used to displace the atmospheric gas in the chamber and to replace it with a predetermined mixture of treatment gas. When the predetermined subatmospheric pressure is reached within the chamber, the patient removes the face mask and breathes the treatment mixture of gas at the predetermined subatmospheric pressure. The excess liquid in the lungs of the patient is evaporated into the treatment gases. The treatment gases are recirculated and exposed to ultraviolet radiation to kill bacteria therein and to prevent the patient from reinfecting himself or herself.

10 Claims, 1 Drawing Sheet

METHOD AND APPARATUS FOR REMOVING LIQUID FROM A PATIENT' S LUNGS

BACKGROUND OF THE INVENTION

The present invention relates to medical devices and methods in general and in particular to a method and apparatus for removing excess liquid from a patient's lungs.

A common cause of excess fluid in the lungs is pneumococcal pneumonia, the most common type of pneumonia. Pneumococci bacteria enter the respiratory passages and make their way to the lungs where they lodge in the bronchioles causing the corresponding alveoli to collapse. The pneumococci breed in the alveoli, creating the inflammatory process that begins with the discharge of protein-rich fluid into alveolar spaces. This fluid serves as a culture medium for the pneumococci and transports them to other lung tissues including alveoli, segments and lobes.

The survival rate for persons treated with pneumococcal pneumonia is considerably higher for younger patients than with older patients and patients receiving early treatment have the best chance of recovery. In some of the cases, surgery is required.

There is a need for a simple non-invasive, but effective, procedure for removing excess pulmonary liquid from the lungs regardless of age.

SUMMARY OF THE INVENTION

The present invention provides a hypobaric or subatmospheric pressure in which the patient is allowed to breathe. The excess pulmonary liquid is evaporated as the patient breathes in the subatmospheric environment.

The prior art includes the Burton U.S. Pat. No. 2,385,683 dated Sep. 25, 1945 which relates to a hypobaric chamber used in treating persons with high blood pressure. The Burton patent does not suggest the use of subatmospheric pressures for the removal of excess pulmonary liquids. Burton similarly does not teach the use of a controlled mixture of gases breathed by the patient.

The prior art also includes the Bancalari U.S. Pat. No. 3,903,869 dated Sep. 9, 1975 which teaches a negative pressure chamber for infants. This patent relates to a specialized chamber for treating infants having Idiopathic Respiratory Distress Syndrome. This patent does not suggest the use of subatmospheric pressure for removing excess lung fluid. Furthermore, this patent teaches the use of negative pressure for enclosing only the thorax and upper abdomen of an infant.

The prior art also includes various hyperbaric chambers for providing a high pressure chamber for treatment of the "bends" or nitrogen narcosis. Examples of this type of mechanism include the Saxon et al U.S. Pat. No. 4,467,798 dated Aug. 28, 1984 and the Krasle U.S. Pat. No. 4,727,870 dated Mar. 1, 1988.

The prior art also includes ultraviolet light sources for purifying air, as for example the Patterson U.S. Pat. No. 3,967,927 dated Jul. 6, 1976.

In contrast to the prior art summarized above, the present invention utilizes a hypobaric chamber wherein a sufficiently reduced pressure is provided so that, as the patient breathes, excess pulmonary liquid in the lungs is evaporated into the low pressure gas mixture inhaled by the patient and exhaled into the chamber. Using this approach, excess pulmonary liquids are effectively removed in a safe, comfortable and non-invasive way.

The present invention also includes a helium purge system for displacing the gases in the hypobaric chamber with little or no pressure differential. A sterilization system is also provided for treating gases in the chamber.

The primary object of the present invention is to provide a safe, comfortable and non-invasive apparatus and method for removing excess pulmonary liquids.

A further object of the invention is to provide a hypobaric chamber for removal of excess pulmonary liquid which also provides a sterilization system located within the chamber to sterilize the exhaled bacteria and to, thereby, prevent reinfection of the patient.

A further object of the invention is to provide a hypobaric chamber for removal of excess pulmonary liquids wherein a helium purge is provided, utilizing little or no pressure differentials to purge the chamber and to allow the introduction of appropriate treatment gases into the hypobaric chamber.

A further object of the invention is to provide a hypobaric chamber for removal of excess pulmonary liquids wherein the patient is provided with a face mask which allows the patient to breathe comfortably while the chamber is being purged.

Other objects and advantages of the invention will be apparent from the following description of the preferred embodiment and the accompanying drawing wherein

BRIEF DESCRIPTION OF THE PREFERRED EMBODIMENT

Figure 1:
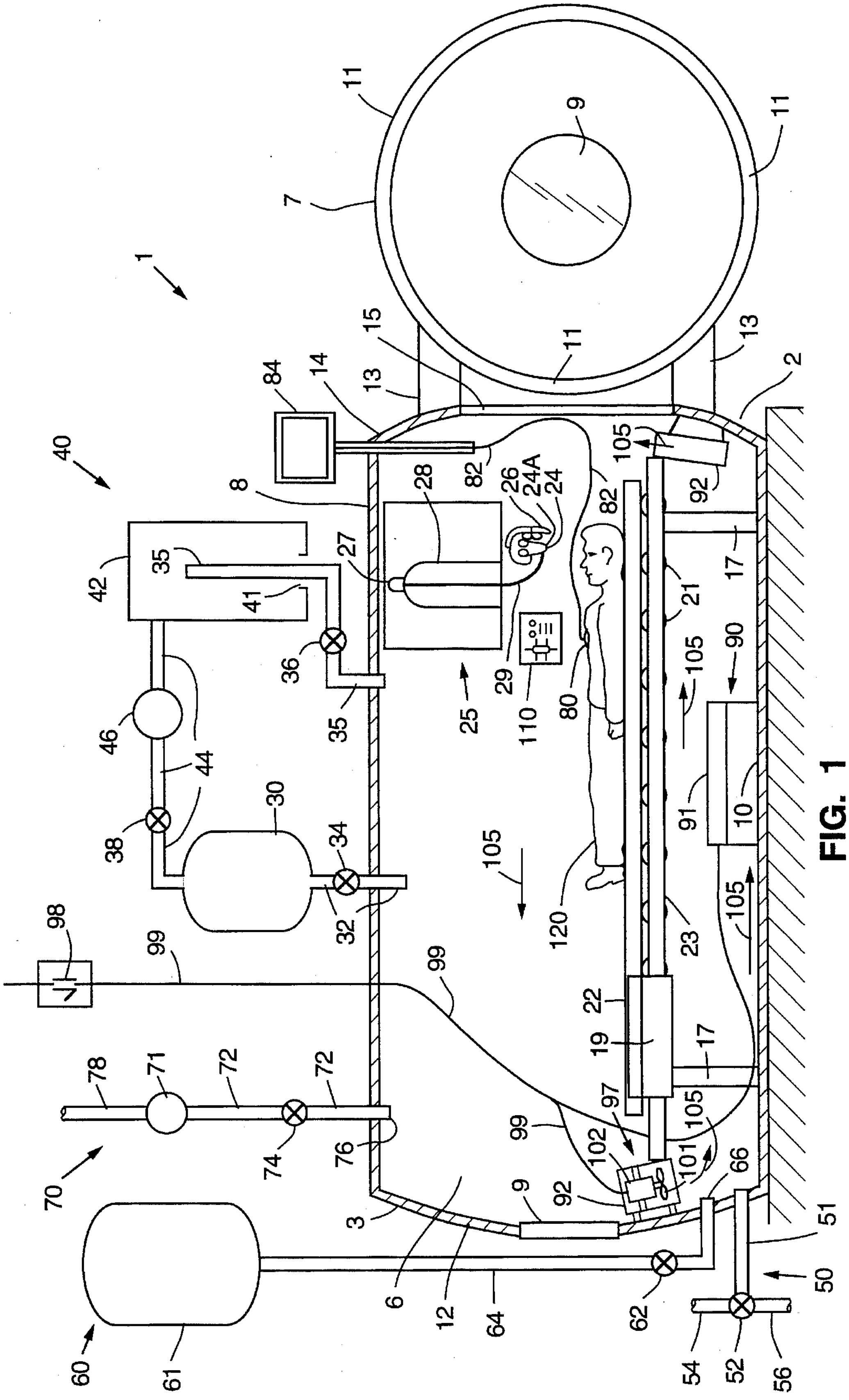
FIG. 1 is a schematic elevational view of the hypobaric chamber according to the present invention shown partially in section.

As shown in FIG. 1, an apparatus shown generally as 1 provides a low pressure environment for the removal of excess pulmonary liquids.

A generally cylindrical vessel 3 is provided which includes upper wall 8, lower wall 10 and an enclosed end wall 12. An open or partial end wall 14 is provided against which a hatch 7 operates to form a fully enclosed and pressure-tight chamber 6. Although the vessel 3 is shown to have a generally cylindrical shape, it can have other configurations without departing from the scope of the present invention.

An opening 15 is formed in end wall 14 which has sufficient size to permit a patient to enter or exit the chamber 6. A hatch 7 is pivotally carried by open end 14 of the vessel 3. The hatch 7 is movable between the open position shown in FIG. 1 wherein a patient may be moved into or out of the vessel 3 and a closed position wherein the hatch 7 forms a pressure-tight seal against the end wall 14 of the vessel 3 and wherein in the closed position the hatch 7 and vessel 3 form a pressure-tight enclosed hypobaric chamber 6.

A sealing strip 11 is provided around the periphery of hatch 7 to engage end wall 14 and to form a seal when hatch 7 is in its closed position. Sealing strip 11 is constructed of elastomeric composition to enhance its sealing capability. Sealing strip 11 may also be constructed of magnetic material whereby the patient in an emergency situation can open the hatch 7 from inside the chamber 6.

A viewing port or window 9 is provided in hatch 7 to permit observation of the patient from outside the vessel 3. Viewing ports or windows may be located in either end wall 12 and 14 or elsewhere on the surface of vessel 3.

A support fixture is provided within chamber 6 including struts 17, frame 19, rollers 21, planar table 22 and table support track 23. Upright struts 17, which support frame 19, are secured to the lower wall portion 10 at their lower end and to frame 19 at their upper end. Guide rollers 21 are rotatably mounted in frame 19 and slidably support table 22 upon which the patient 120 is positioned. In this way, the patient can be readily moved into and out of chamber 6 by sliding the table 22 on rollers 21. Table 22 is dimensioned to fit through opening 15 and position to be aligned therewith and held in place by table support track 23. The width of frame 19 is less than the width of vessel 3 so that there is ample room for gases to be circulated during treatment as discussed in greater detail below. Table 22 may be provided with an adjustable feature, not shown, which would allow the elevation of a portion of the table.

A conventional breathing apparatus 25 is provided which incorporates a demand regulator valve 24 and a built-in communication system **24*a*. The breathing apparatus 25 also includes a face mask 26 and a gas tank 28 which contains an oxygen-rich gas mixture. The oxygen-rich gas mixture is fed through gas feed line 29. The gas mixture is delivered to the patient at the ambient pressure which exists in chamber 6 at any moment in time via the demand regulator valve 24 so that the oxygen-rich mixture of gas is provided throughout the pressure ranges used within chamber 6, in the range of 2 to 15 psi. Gas tank 28 is releasably mounted to the support frame 27 which is secured to the interior wall of vessel 3**.

Although the chamber is capable of operating throughout a wide range of pressures, it is anticipated that most of the use of the chamber would be performed at pressures below 10 psi which is the approximate pressure level at which relatively healthy persons are able to breathe comfortably without the use of a face mask.

A gas sterilization means shown generally as 90 is mounted in the lower wall portion 8 of the chamber 6. The gas sterilization means 90 includes an ultraviolet light source 91 which is secured to the lower wall 10. The sterilization system 90 can be located elsewhere in the chamber 6 without departing from the present invention. Light source 91 emits ultraviolet radiation and a wavelength of 200 nanometers and above in order to kill bacteria released into the vessel 3 by the patient 120. Ducting 92 is provided to control the flow of the gases through chamber 6. The fan system which is generally designated 97 is provided with blades 101 and motor 102 draws gases from the dorsal portion of chamber 6 through the ducting 92 and thereby past the ultraviolet light source 91 thereby sterilizing the said gases. The reasons for the sterilization process include prevention of reinfection of the patient 120 and also the protection of the health of the staff and of the general population. The gas flow is generally shown by arrows 105. Power for ultraviolet radiation light source 91 and electric motor 102 is provided by power line 99 connected to a suitable power source (not shown). The motor 102 and light source 91 are activated by closing switch 98 schematically shown in FIG. 1.

A conventional monitoring system is provided to monitor the condition of the patient which includes, for example, the patient's heart rate and other critical parameters depending upon the patient's condition. Sensors 80 can be attached to the patient for sensing heart rate. Signals are transmitted along lines 82 to monitor 84 where the patient's condition is visually monitored. The chamber in the preferred embodiment is provided with a conventional intercom system, schematically shown as 110, so that the patient may communicate with persons outside the chamber 6. A voice communication device may also be provided in said face mask as a back-up communication system.

A gas circulation system 60 includes a storage tank or vessel 61 for storing the treatment gases under pressure. The storage tank or vessel 61 is releasably mounted so desired treatment gas mixtures may be changed as directed by the physicians in charge for different patients.

In general, the treatment gas mixtures will comprise 50–99.95% oxygen, 0.05–0.20% carbon dioxide and nitrogen between 0.00–49.95%. The treatment gas mixture flows from the tank or vessel 61 through treatment gas line or conduit 64 to control valve 62 for varying the flow rate therethrough. Control valve 62 has an outlet which communicates through conduit 66 to the interior of chamber 6.

Exchange means 50 includes a conduit 51 and threeway valve 52 positioned adjacent the lower wall portion 10. Exchange means 50 communicates through conduit 51 with the interior of the vessel 3 to allow the downward displacement and exhaust of gases from vessel 3 caused by the helium purge discussed below. Threeway valve 52 will close exchange pipe 51 to prevent gas flow therethrough. In its second position, valve 52 permits gases to be introduced into chamber 6 through conduit 54. In its third position, valve 52 permits gases to be discharged from chamber 6 through exhaust port 56.

A vacuum pump means 70 is provided for evacuating gases from the chamber 6 in an amount sufficient to reduce the pressure in vessel 3 to the desired treatment pressure. Vacuum pump means 70 includes a conventional pneumatic pump 71 and exhaust conduit 72 which communicates with the interior of vessel 3. Exhaust line 72 has an inlet port 76 in the vicinity of the upper wall portion 8. Control valve 74 is coupled to line 72 for controlling gas flow therethrough. Discharge conduit or line 78 extends from pump 71 for discharging the gases to be evacuated from chamber 6. Thus, when pump 71 is energized and valve 74 is in its open position, gas line 72 carries gases from chamber 6 to pump 71 where they are discharged through line 78.

The preferred embodiment of the invention further comprises a helium gas purge means 40. The helium purge means 40 is utilized to replace the atmospheric air in chamber 6 with helium and then to replace the helium with a predetermined mixture of treatment gases stored in tank 61. Helium purge means 40 comprises an inlet conduit 32 communicating with the interior of vessel 3 and extending upwardly to a helium pressure storage tank 30. An exhaust conduit 35 extends upwardly from upper wall portion 8 into helium scavenging tank 42. Scavenging tank 42 has a gas vent 41 for the purpose of preventing pressure differential conditions resulting during the process of gas transfer exchange. Helium pressure tank 30 is filled with pressurized helium gas. Control valve 34 is coupled to line 32 for controlling the flow rate of helium gas from tank 30 into chamber 6 through line 32. Similarly, control exhaust valve 36 is coupled to line 35 to control the flow rate of helium gas from chamber 6 into the helium scavenging tank 42. A return cycle line or conduit 44 connects the helium scavenging tank with pressurized helium storage tank 30. Control valve 38 is carried to line 44 for pumping helium gas from scavenging tank 42 to storage tank 30 through line 44. In this way, the helium is recycled and the storage tank 30 is readily refilled and pressurized by pump 46.

In operation, the patient having excess pulmonary liquid is positioned on table 22 and moved into chamber 6. The hatch 7 is closed. The chamber 6 initially contains atmospheric gases at the standard atmospheric pressure of about 15 psi and standard temperature. The air comprises a mixture of approximately 78% nitrogen, 21% oxygen and trace amounts of argon, carbon dioxide, neon, helium and other gases. When hatch 7 is closed, the patient is in a pressure-tight chamber 6. The patient places face mask 26 over his or her face and proceeds to breathe the air or oxygen-rich mixture provided from tank 28 at the ambient pressure existing in chamber 6 at the instant of delivery through the demand regular valve 24.

Helium gas is then introduced into chamber 6 to displace the atmospheric gases present in the chamber. Exchange means 50 is activated by opening valve 52 to permit the atmospheric gas to be exhausted from the chamber 6 at its lower portion through lines 51 and 56. Control valve 34 is open so that helium gas from tank 30 enters the chamber 6 from the upper region of the chamber at a rate that minimizes turbulent mixing with the atmospheric gases. A baffle (not shown) can be used to this effect. The less dense helium gas forms a separate distinct gas phase and displaces the atmospheric gases downwardly towards exchange means 50. The helium is at substantially the same pressure as the gas in the vessel. By "substantially the same," we mean within 10%. Sufficient helium gas is introduced into chamber 6 to completely displace the atmospheric gases.

After the atmospheric gases have been displaced and discharged, valves 34 and 52 are closed. Valve 36 which controls the helium flow through line 35 into the scavenging tank 42 is then opened. Valve 62 controlling the treatment gas flow is open to allow the mixture of treatment gases into chamber 6 at a rate which minimizes turbulent mixing with the helium. The higher density treatment gases are supplied to the chamber 6 in an amount sufficient to displace the lighter helium gas completely from chamber 6 through line 35 and into helium scavenging tank 42. The treatment gases provide sufficient oxygen and carbon dioxide to the patient so that the patient can breathe comfortably under hypobaric conditions. The specific percentages of these gases in the mixture will depend upon the relative condition of the patient.

When all of the helium gas has been evacuated from the inside of chamber 6, treatment gas valve 62 and helium discharge valve 36 are closed to seal chamber 6. The pressure of the mixture of treatment gases within chamber 6 is controlled through the operation of vacuum pump means 70. Pump 71 is activated and gas valve 74 opened to permit treatment gases to be evacuated from chamber 6 through line 72. The pumping operation is continued until a sufficient amount of the treatment gases has been evacuated from chamber 6 so that the pressure is reduced to a desired subatmospheric or hypobaric pressure which will be typically in the range of from 2 to 12 psi, although most treatments would typically require pressures below 10 psi. The pressure within chamber 6 is monitored with conventional pressure gauges (not shown). Valve 74 is closed at the desired pressure.

When the designated hypobaric pressure has been reached, the patient removes face mask 26 and is allowed to breathe the treatment gases. As the patient breathes, the excess pulmonary liquid in the patient's lungs is evaporated and transferred into the gases inhaled by the patient and exhaled into chamber 6. The ultraviolet light source 91 as well as fan 97, motor 102 and sterilization system 90 are activated to kill the bacteria exhaled by the patient.

The treatment time will normally vary anywhere between 1 to 24 hours. When the treatment is completed, the patient replaces face mask 26 and breathes the oxygen-rich mixture from tank 28. Threeway valve 52 is positioned to permit the treatment gases to be discharged from the chamber and helium control valve 34 is opened. The helium is introduced in an amount sufficient enough to remove the treatment gases from the interior of chamber 6 through exhaust means 50. After the treatment gas has been completely removed from chamber 6, helium control valve 34 and threeway valve 52 are closed and the recirculation valve 36 is opened. Valve 52 is then repositioned to allow atmospheric gases to enter into the chamber through lines 51 and 54. The atmospheric gases will displace the helium into the helium scavenging tank 42 through conduit or line 35.

The patient can then remove face mask 26 and exit the chamber 6 through the opening 15. The helium gas is prepared for reuse by opening refill valve 38 and actuating helium pump 46 to cause the helium gas to flow from scavenging tank 42 through the refill line 44 and into the helium storage tank 30. When all the helium gas has been exhausted from the helium scavenging tank 42, pump 46 is shut off and helium refill valve 38 is closed. In this manner, storage tank 30 is refilled with helium for another flushing or purging operation.

The above is a detailed description of the preferred embodiment of the invention. It is recognized that departures from the disclosed embodiment may be made within the scope of the invention and that obvious modifications will occur to a person skilled in the art.

What is claimed is:

1. A hypobaric chamber for evaporating excess fluid from the lungs of a patient comprising:

a vessel having an enclosed end an open end and a lower wall, a hatch carried by said open end, said hatch movable between an open position, wherein a patient may be moved into or out of said vessel, and a closed position, wherein said hatch forms a pressure tight seal against said vessel and wherein said hatch and vessel form a pressure tight enclosed chamber, vacuum pump means communicating with the interior of said vessel for reducing the pressure in said vessel to a predetermined subatmospheric pressure, a helium purge means communicating with the interior of said vessel for purging said vessel by allowing helium to flow into said vessel and to displace the gases in said vessel, exchange means communicating with the interior of said vessel through the lower wall of said vessel to allow the downward displacement and exhaust of gases in said vessel, a face mask, means for supplying the patient with an oxygen-rich gas to breathe through said face mask as the pressure in the chamber is reduced, and means for filling said chamber with a treatment gas after the chamber has been purged, comprising 50 to 99.95% oxygen, 0.05 to 0.20% carbon dioxide and 0 to 49.95% nitrogen, whereby said patient removes said mask and breathes said treatment gases, and said excess fluid in the patient's lungs evaporates into said treatment gases.

2. The apparatus of claim 1 wherein said helium gas purge means displaces gases within said vessel downwardly with helium wherein the helium gas is at substantially the same pressure as the gas being displaced.

3. The apparatus of claim 2 wherein said helium purge means includes a helium scavenging tank, a pressurized helium storage tank, and a control valve and pump between said scavenging and storage tanks whereby the helium may be recycled and reused to purge said gases in said vessel.

4. The apparatus of claim 1 wherein said means for supplying the patient with oxygen-rich gas comprises a pressurized supply tank of oxygen-rich gas, said face mask worn by said patient, a feed line connected between said tank and said face mask, and a demand regulator in said feed line whereby said oxygen-rich gas is supplied to the patient at the ambient pressure existing within said chamber at any moment in time.

5. The apparatus of claim 1 wherein said vessel is cylindrical in shape.

6. The apparatus of claim 5 further comprising magnetic sealing strips located between said hatch and said vessel whereby said hatch may be opened from inside said vessel.

7. A method for removing excess pulmonary liquid from the lungs of a patient comprising the steps of:

placing a patient having excess pulmonary fluid in an enclosed chamber, reducing the pressure in said enclosed chamber to a predetermined subatmospheric pressure in the range of 2 to 10 pounds per square inch, providing the patient with an oxygen-rich supply of gas at a controlled pressure through a face mask as the pressure in said chamber is being reduced, filling said chamber with a mixture of treatment gases at said predetermined subatmospheric pressure including 50 to 99.95% oxygen, 0.05 to 0.20% carbon dioxide and 0 to 49.95% nitrogen, removing the face mask from the patient, and allowing the patient to breathe said treatment gases at the reduced pressure, whereby said excess pulmonary fluid is evaporated into said treatment gases.

8. The method of claim 7 comprising the further step of purging said chamber with helium by allowing helium to enter the upper portion of said chamber at substantially the same pressure as the pressure of the gas in the chamber, and the gas in the chamber is displaced downwardly through an exhaust conduit located at the lower portion of said chamber.

9. The method of claim 8 comprising the further step of:

displacing said helium gas upwardly and out of said chamber with a treatment gas, and recovering said helium for future use in purging said chamber.

10. The method of claim 7 wherein said oxygen-rich gas is supplied to said patient at the pressure of the ambient gas in said chamber at that moment.

* * * * *